United States Patent [19]
Clarren

[11] Patent Number: 4,776,324
[45] Date of Patent: Oct. 11, 1988

[54] THERAPEUTIC AND PROTECTIVE INFANT HELMETS

[75] Inventor: Sterling K. Clarren, Seattle, Wash.

[73] Assignee: The Children's Orthopedic Hospital and Medical Center, Seattle, Wash.

[21] Appl. No.: 40,365

[22] Filed: Apr. 17, 1987

[51] Int. Cl.[4] .................................................. A61F 5/00
[52] U.S. Cl. .................................... 128/76 R; 128/380
[58] Field of Search ................. 128/76 R, 76 B, 76 C, 128/76 D, 380; 2/171.2

[56] References Cited

PUBLICATIONS

Head Circumference/Boys and Girls, Ref: Nellhaus, G., Composite International & Interracial Graphs, Pediatrics 41:106, 1968, supplied by Mead Johnson Laboratories.
Clarren, S. K., et al., "Helmet Treatment for Plagiocephaly and Congenital Muscular Torticollis," The Journal of Pediatrics, 94(1):43–46, 1979.
Clarren, S. K., "Plagiocephaly and Torticollis: Etiology, Natural History, and Helmet Treatment," The Journal of Pediatrics, 98(1):92–95, 1981.
James, H. E., et al., "A Multipurpose Infant Helmet," Concepts Pediat. Neurosurg., 5:41–47, (Karger, Basel 1985).

*Primary Examiner*—Charles Pearson
*Assistant Examiner*—Tonya Lamb
*Attorney, Agent, or Firm*—Christensen, O'Connor, Johnson & Kindness

[57] ABSTRACT

A method of helmet treatment for deformational cranial asymmetry in which the dimensions of the therapeutic helmet cavity are prescribed in relation to specific CT scan sections of the plagiocaphalic infant's cranium. A graded series of sized helmets is provided for such treatments. Each helmet cavity is configured to accommodate and effectively treat infants of specified ages and degrees of plagiocephaly. By employing the subject off-the-shelf helmets, the time-consuming and labor-intensive fitting of individualized helmets is obviated.

9 Claims, 3 Drawing Sheets

THERAPEUTIC AND PROTECTIVE INFANT HELMETS

FIELD OF THE INVENTION

This invention relates to orthopedics, particularly to therapeutic helmets for treating plagiocephaly and for postoperative protection of the infant cranium.

BACKGROUND OF THE INVENTION

Referring to FIG. 1, the cranium 10 or brain case of a human infant is made up of frontal 12, parietal 14, temporal 16, and occipital 18 bones that encase and protect the brain (not shown). These bones are separated by membranous intervals 20 until brain growth is complete, at about eighteen to twenty-four months of age. During that time period, pediatricians routinely monitor the accompanying growth of the cranium by measuring the maximum circumference of the cranium 10, the so-called occipital-frontal circumference 22 that goes around the cranium 10, for comparison with tabulated average values for the population. See, for example, Nellhaus, G., Composite International and Interracial Graphs, Pediatrics 41: 106, 1968, hereby incorporated by reference. During the first eighteen months of age, the mean head circumference 22 increases from about 34 to about 48 cm for boys, and from about 34 to about 47 cm for girls. After about twenty-four months of age, thickening of the cranial bones accounts for subsequent head growth.

Referring to FIG. 2, two additional reference lines are commonly established with respect to the infant cranium 10. A midsagittal line 24 runs through the mandibular symphysis 26 and the interpupillary midpoint 28. Extending line 24 back through the inion 29, the most prominent point of the external occipital protuberance, defines the midsagittal plane 30 that, in a normal infant, bisects the cranium 10 into substantially exact halves. As discussed below, judgments concerning cranial symmetry or asymmetry are typically made with reference to plane 30.

As also shown in FIG. 2, for the purpose of orienting the head for cranial computed tomography (CT), a transverse plane 32 is established through a pair of supraorbital-meatal reference lines or baselines 34, which typically run through the supraorbital arch 36 and the external auditory meatus 38 on either side of the cranium 10. Referring now to FIG. 3, an infant's cranium 10 is shown in a section view taken along the midsagittal plane 30 as in a standard Horz (LAT) pilot scan in cranial computed tomography. Representative transverse planes 34a–i are shown parallel to the supraorbital-meatal baseline 34. Such transverse planes 34a–i conform with the standard CT brain "slices" that are taken for various diagnostic purposes. For example, see A. G. Lurus, et al., CT Application Guide, Picker International, 595 Miner Road, Highland Heights, Ohio, hereby incorporated by reference.

As mentioned, the normal infant cranium 10 is symmetrical with respect to midsaggital plane 30. However, a condition known as plagiocephaly, characterized by a rhomboid-shaped head, occurs in at least one in 300 live born infants. Such cranial asymmetry usually results from late gestational or postnatal deformation. When an infant's rapidly growing head is maintained in a nearly fixed position against the uterine wall or the mattress, the cranium 10 progressively flattens. Such deformational plagiocephaly generally will improve within a few months after birth, especially if a full range of neck movement can be rapidly achieved. However, for perhaps ten percent of affected infants, plagiocephaly may persist into adulthood as a permanent, mild-to-severe cosmetic disability.

Applicant previously reported that individualized plastic helmets could remold the rhomboid-shaped head into a more usual form. Clarren, S. K., et al., The Journal of Pediatrics 94(1): 43–46, 1979. In that preliminary study, individually fitted plastic helmets, similar in style to football helmets, were designed to fit snugly against the prominent aspects of an infant's cranium and to be loose fitting where the head is shallow. The patients wore their helmets continuously for two to three months. Cranial asymmetry dramatically improved as the patient's brain grew and the head filled out the helmet and thus acquired a more usual shape. Again, such helmets were individually fitted, that is, made from a precise impression of each patient's plagiocephalic cranium. A thin cotton cap was placed over the patient's head, and this was then covered with plaster to make a cast. After the cast had been removed and thoroughly dried, a replica of the patient's head shape was obtained for filling the cast with modeling clay or plaster of Paris. The cast was then cut away and discarded. Modeling clay or plaster slurry was then used to build up the flattened areas of the model head until a more ideal shape was achieved. No additions were placed over the prominent aspects of the model so as to assure a snug helmet fit in those areas. The occipitofrontal circumference was increased by no more than 3 cm, as otherwise the helmet was reportedly too loose for effective wear. Standards for growth in head height were not available, but allowance for growth in this plane was also required and was estimated. A polypropylene sheet was then vacuum formed over this individually sculpted mold to produce the particular patient's helmet.

Applicant subsequently reported the results of additional helmet treatments, using the above-described individually fitted helmets, in which an attempt was made to objectify the degree of plagiocephaly through standard superior and frontal photographs of each potential subject's head. Such photographic measures were reportedly arbitrary and prone to some error. Clarren, S. K., The Journal of Pediatrics 98(1): 92–95, 1981.

Of less direct interest, other than their off-the-shelf availability, are protective helmets that employ adjustable padding to suspend the cranium within the helmet cavity. Such bicycle-type helmets have been employed for children following cranial reconstructive surgery. H. E. James, et al., Concepts pediat. Neurosurg. 5: 41–47, 1985.

It would be advantageous, for treating plagiocephaly, to provide helmets that need not be individually molded and fitted. It would also be advantageous to provide an improved off-the-shelf helmet for protecting infants who are at risk for brain injury from minor trauma, such as following cranial surgery.

SUMMARY OF THE INVENTION

The invention provides, in one aspect, a method of helmet treatment for deformational cranial asymmetry in which the dimensions of the therapeutic helmet cavity are prescribed in relation to specific CT scan sections of the infant's cranium. A graded series of sized helmets is provided for such treatments. Each helmet cavity is configured to accommodate and effectively treat infants of specified ages and degrees of plagiocephaly. By employing the subject off-the-shelf helmets, the time-consuming and labor-intensive fitting of individualized helmets is obviated.

To prescribe an appropriate therapeutic helmet, horizontal and transverse CT scans are made of the plagiocephalic infant's cranium. The transverse scans are generated parallel to a supraorbital-meatal baseline. From among the transverse scans, the section having the cranial outline with the longest anterior-posterior dimension is selected. Certain critical helmet dimensions are measured from this selected section, as described below, including the maximum circumference, maximum lateral axis, anterior-posterior axis, and maximum chord. From a horizontal CT scan, the maximum height of the helmet cavity is taken. A helmet is then prescribed for the infant's treatment having a cavity that substantially conforms in shape to a normal infant cranium and that is dimensioned to at least equal and exceed by no more than 4 and preferably 2 cm the corresponding measured values of the plagiocephalic cranium. The availability of a graded series of sized helmets permits the attending physician to prescribe and order an appropriate therapeutic helmet, on the basis of data generated from standard CT scans, from a location remote from the helmet manufacturer and distributor.

DETAILED DESCRIPTION OF THE PREFERRED EMBODIMENT

The invention provides, in one aspect, a method of helmet treatment for deformational cranial asymmetry in which the dimensions of the therapeutic helmet cavity are prescribed in relation to specific CT scan sections of the infant's cranium. A graded series of sized helmets is provided for such treatments. Each helmet cavity is configured to accommodate and effectively treat infants of specified ages and degrees of plagiocephaly. By employing the subject off-the-shelf helmets, the time-consuming and labor-intensive fitting of individualized helmet is obviated. Furthermore, since the subject helmets are prescribed on the basis of data generated from standard CT scans, the attending physician can prescribe and order a suitable helmet, from a location remote from the helmet manufacturer or distributor, with relatively minor inconvenience and expense to the patient and patient's family.

Figure 1:
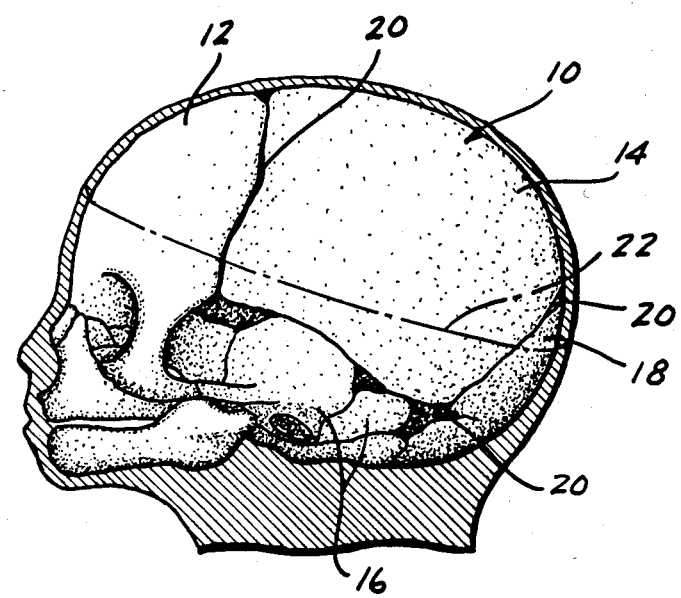
FIG. 1 is a lateral view of the human skull at birth showing the bones that make up the cranium and indicating the maximum occipital-frontal circumference by which head growth is conventionally monitored.
Figure 2:
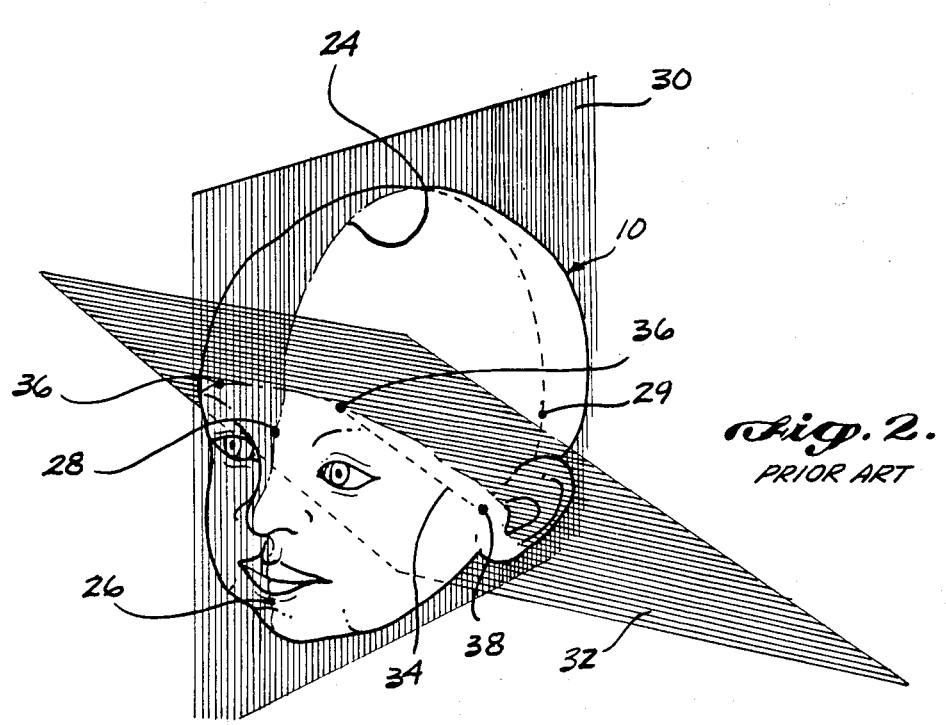
FIG. 2 is an oblique view of an infant's head illustrating two reference planes, the midsaggital plane and a transverse plane parallel to a supraorbital-meatal baseline, that are commonly used to assess cranial symmetry and orient the head for CT scanning, respectively.
Figure 3:
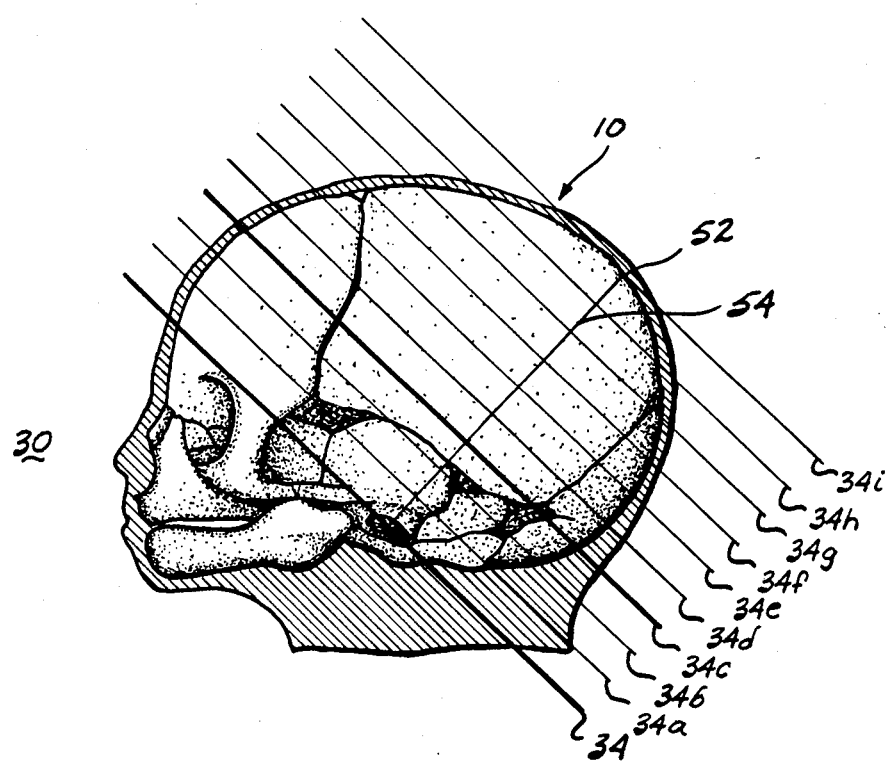
FIG. 3 is another lateral view of the infant skull illustrating the locations of representative transverse planes, parallel to a supraorbital-meatal baseline, that conform with standard CT brain scan views, and furthermore showing how the subject helmet height dimensions is determined.

Standard procedures are followed for the CT scanning. The infant is positioned supine, nose up, with the head placed securely in a head holder. The midsagittal line 24 (but, for the plagiocephalic patient, not necessarily the inion 29 and plane 30) is aligned with the instrument's midline laser. The instrument's horizontal laser is aligned conventionally with the interpupillary midpoint 28. A horizontal or lateral scan is made with the horizontal laser centered at the mandibular symphysis 26, to produce a view such as shown in FIG. 3. Representative slices through transverse planes 34 to 34i are then taken after aligning the tilt line parallel with the supraorbital-meatal baseline 34, which in this embodiment passes through the supraorbital arch 36 and the external auditory meatus 38. Other baselines 34, such as a baseline 34 used to generate brain slices at an angle of about 20° cephalad from the orbital-meatal line, can alternatively be employed here. Transverse planes 34a–i can be on the order of eight to ten millimeters apart, and uniform slice thicknesses of that magnitude can be set with the instrument. The superior limit, or last slice 34i, is typically set at the vertex 52 of the cranium 10. Following this procedure, the horizontal scan and transverse views are developed in standard fashion.

Pursuant to the invention, data from the standard CT scans are used to assure that the following critical helmet dimensions are met. From the horizontal scan, the maximum height (MH) of the infant's cranium 10 is measured along the line 54 (FIG. 3), perpendicular to the supraorbital-meatal baseline 34, that intersects the vertex 52, that is, the longest such line 54 that can be drawn perpendicular to baseline 34 within the confines of the cranium 10.

Figure 4:
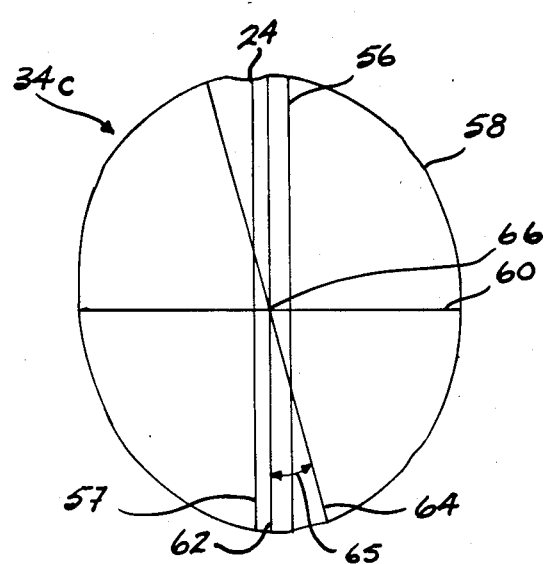
FIG. 4 is a schematic view of a representative transverse CT brain scan of a plagiocephalic patient, showing how the other critical helmet dimensions are determined.

The other critical helmet dimensions are measured from the transverse section, parallel with the supraorbital-meatal baseline 34, that has the greatest anterior-posterior dimension. A representative section 34c is shown in FIG. 4. The maximum anterior-posterior dimension 56, parallel to the plane 57 that results from alignment of the instrument's midline laser with midsagittal line 24, is measured within this section 34c. That dimension 56 is then compared with similar dimensions 56 in the other sections to select the section (34c, in this illustrative embodiment) from which to prescribe the additional helmet dimensions. For most plagiocephalic infants, the third to fifth, and typically the fourth section superior to baseline 34, assuming 10-mm slice thicknesses, will have the greatest anterior-posterior dimension 56 and so can be used to prescribe the other helmet dimensions.

Once selected, the circumference 58 of the section 34c is measured to define the maximum circumference 58 (MC) of the infant's cranium 10 parallel to the transverse plane 32. The maximum (i.e., longest) lateral axis (ML) 60, perpendicular to plane 57, is also selected and measured. Then the anterior-posterior axis (AP) 62 perpendicular to and bisecting the maximum lateral axis 60 is selected and measured. Next, the maximum chord (mc) 64 passing through the intersection 66 of the maximum lateral axis 60 and the anterior-posterior axis 62 is selected and measured, and the chord angle 65 with respect to axis 62 is measured.

Figure 5:
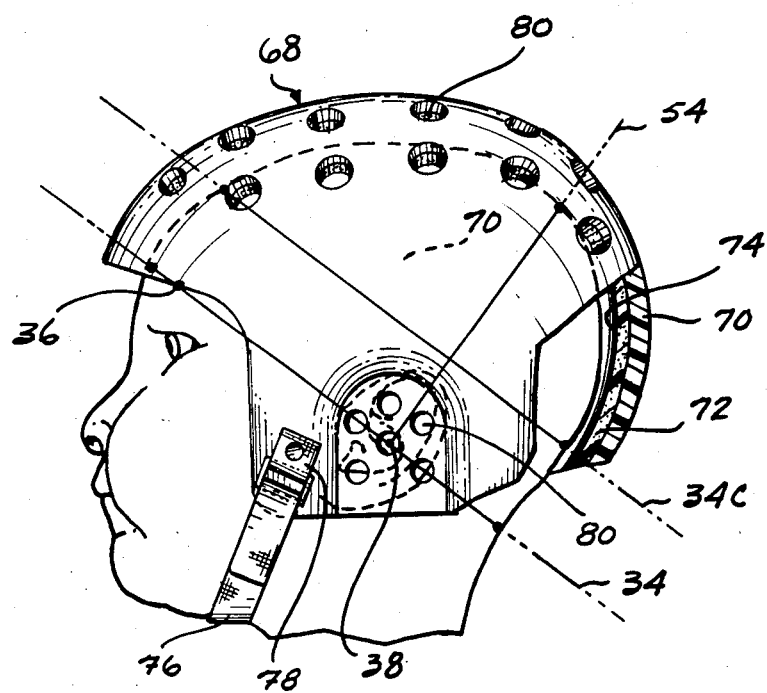
FIG. 5 is a schematic section through a representative therapeutic helmet of the invention; and, FIG. 6 is a view similar to FIG. 4 but showing a preferred method of determining the maximum diagonal chord for fitting the subject helmet.

From the foregoing measurements, a helmet 68 for the plagiocephalic infant's treatment is prescribed. A representative helmet 68 is shown in FIG. 5. Helmet 68 is shaped in outward appearance much like a football or bicycle helmet, having an outer shell 70 of lightweight, high-impact material such as polypropylene and/or a cellular plastic 72. However, the helmets 68 of this invention lack the internal padding of such conventional protective helmets, which padding is typically adjustable to suspend the cranium substantially uniformly within a cushioning airspace within the helmet. In contrast, the internal cavity 74 of the subject helmet 68 is designed to substantially conform in shape to a normal infant cranium and furthermore has a maximum circumference, maximum lateral axis, anterior-posterior axis, maximum chord, and maximum height at least equal to and not more than about four cm greater than the foregoing values measured from the infant's CT scans. The subject helmet 68 will also typically be provided with a chin strap 76 and associated fasteners 78, and with a plurality of air holes 80 for ventilation.

In another aspect, the invention provides a graded series of sized helmets 68 ranging in maximum circumference 58 from about forty to about fifty-two centimeters, in one- or two-centimeter intervals. Such a sized series is selected to encompass the tenth to ninetieth percentiles of infant head size at the age levels spanning ten to eighteen months. These standard helmets 68 are made from helmet prototypes using conventional manufacturing techniques, such as by pneumatic thermoforming. The helmet prototypes can be fabricated from molds of the heads of normal control infants. Selection of the controls is based upon two criteria. First, a control infant's cranium 10 must not exhibit plagiocephaly, that is, the control cranium 10 must be symmetrically shaped about the midsaggital plane 30. Second, the occipital-frontal circumference 22 of normal infants who meet the first criterion should be measured, as a rough index of the disclosed circumference 58, in order to select a graded series of controls that approximately exhibit the aforementioned one- or two-centimeter intervals between the tenth and ninetieth percentiles. A plaster cast is made of the cranium 10 of each selected normal infant, and from that cast a plaster prototype of the cranium 10 is made. Confirmation of the suitability of the assembled normal prototypes, for achieving the requisite fit and effective treatment when prescribed as disclosed herein, is made by preparing standard CT scans of the plaster prototypes, using the same orientations as if the prototypes were actual craniums 10. From the resulting data, final helmet prototypes are selected which conform with each of the following graded sizes.

| Size | MC | ML | AP | mc | MH |
|---|---|---|---|---|---|
| 1 | 40 | 10.3 | 14.0 | 13.75 | 9 |
| 2 | 41 | 10.7 | 14.3 | 14.25 | 9 |
| 3 | 42 | 11.0 | 14.5 | 14.50 | 9 |
| 4 | 43 | 11.3 | 14.8 | 14.75 | 10 |
| 5 | 44 | 11.7 | 15.3 | 15.00 | 10 |
| 6 | 45 | 12.0 | 15.8 | 15.75 | 10 |
| 7 | 46 | 12.3 | 16.3 | 16.25 | 10 |
| 8 | 47 | 12.7 | 16.8 | 16.50 | 10 |
| 9 | 48 | 13.0 | 17.0 | 16.75 | 10 |
| 10 | 49 | 13.0 | 17.3 | 17.00 | 10 |
| 11 | 50 | 13.3 | 18.0 | 17.75 | 10 |
| 12 | 51 | 13.5 | 18.4 | 18.00 | 11 |
| 13 | 52 | 14 | 18.8 | 18.50 | 11 |

Once the graded normal prototypes are selected, as described above, the prototypes can serve as the templates for large-scale manufacture of therapeutic helmets 68 having cavities 72 of the stated dimensions. Representative manufacturing techniques include thermoforming and other plastic molding methods known in the art.

A physician, even at a location remote from the plagiocephalic infant patient, can prescribe a helmet 68 from the foregoing series on the basis of a standard CT series of the patient's cranium 10. After measuring the critical dimensions from the patient's CT scans, as described above, the appropriate helmet is selected which has each of the listed dimensions at least equal to and no more than four centimeters greater than the measured dimensions. Preferably, the listed dimensions should each exceed the measured dimensions by no more than two cm, in order to avoid unnecessary looseness of fit and to assure that the treatment will be completed as rapidly as possible.

Figure 6:
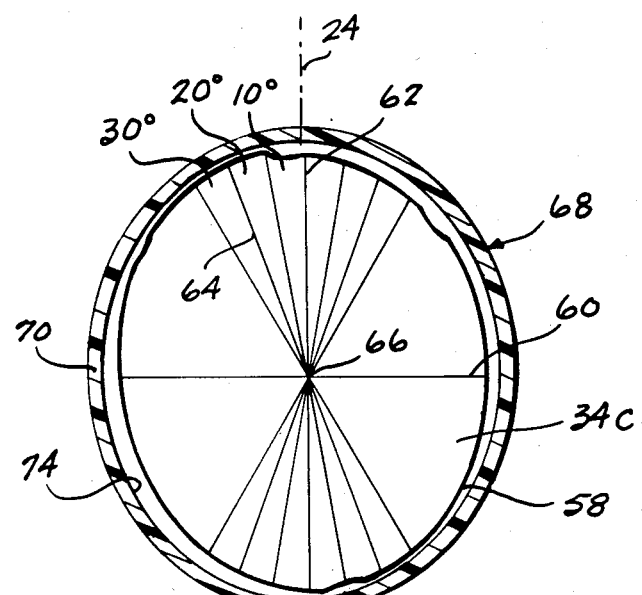

Referring now to FIG. 6, in a preferred embodiment the maximum chord 64 is selected from the group of six chords passing 10°, 20°, and 30° on both sides of the anterior-posterior axis 62 in the transverse section 34c having the geatest circumference 58. From the patient's CT scan data, a helmet is selected having a cavity with at least the following corresponding dimensions, none of which can exceed the patient-specific dimensions by 4 cm, and preferably by no more than 2 cm.

| | | | | mc | | | |
| Size | MC | ML | AP | 10° | 20° | 30° | MH |
|---|---|---|---|---|---|---|---|
| 1 | 40 | 10.3 | 14.0 | 13.75 | 13.50 | 13.25 | 9 |
| 2 | 41 | 10.7 | 14.3 | 14.25 | 13.75 | 13.5 | 9 |
| 3 | 42 | 11.0 | 14.5 | 14.5 | 14.25 | 14.0 | 9 |
| 4 | 43 | 11.3 | 14.8 | 14.25 | 14.25 | 14.0 | 10 |
| 5 | 44 | 11.7 | 15.3 | 15.00 | 14.75 | 14.50 | 10 |
| 6 | 45 | 12.0 | 15.8 | 15.75 | 15.5 | 15.25 | 10 |
| 7 | 46 | 12.3 | 16.3 | 16.25 | 16 | 15.5 | 10 |
| 8 | 47 | 12.7 | 18.8 | 16.5 | 16 | 15.75 | 10 |
| 9 | 48 | 13.0 | 17.0 | 16.75 | 16.5 | 16.5 | 10 |
| 10 | 49 | 13.0 | 17.3 | 17.0 | 16.75 | 16.0 | 10 |
| 11 | 50 | 13.3 | 18.0 | 17.75 | 17.50 | 17.25 | 10 |
| 12 | 51 | 13.5 | 18.4 | 18.0 | 17.5 | 17.0 | 11 |
| 13 | 52 | 14 | 18.8 | 18.5 | 18.0 | 17.75 | 11 |

For convenience, reference can be similarly made to other chord angles (measured as indicated by reference numeral 65 in FIG. 4), such as 15° and 25° on either side of the anterior-posterior axis 62 in section 34c, in order to size the off-the-shelf helmet to the individual patient.

While the invention has been described with reference to data generated by cranial computed tomography (also known as computerized axial tomography, CAT), any imaging technique that can delineate the shape of the cranium as set forth above can be used to practice this invention. Such alternative imaging techniques include nuclear magnetic resonancy (NMR), or even particle emission tomography (PET) scanning.

Following certain neurological procedures, especially when bone is not replaced over the dura, postoperative protection may be required. The subject infant helmets 68 can advantageously provide such protection, and are preferable to bicycle-type helmets, as helmets 68 are lighter in weight, closer fitting and hence less clumsy to wear, and are better tolerated by infant patients.

While the present invention has been described in conjunction with a preferred embodiment, one of ordinary skill after reading the foregoing specification will be able to effect various changes, substitutions of equivalents, and alterations to the subject matter set forth herein. It is therefore intended that the protection granted by Letters Patent hereon be limited only by the definitions contained in the appended claims and equivalents thereof.

The embodiments of the invention in which an exclusive property or privilege is claimed are defined as follows:

1. In a method of helmet treatment for plagiocephaly by fitting an infant having a deformed cranium with a plastic helmet, similar in style to a football helmet, designed to fit snugly against prominent aspects of the deformed cranium and be loose fitting where the head is shallow, and causing the infant to wear the helmet for a period of time sufficient for the deformed cranium to mold to fit the helmet and thereby acquire a more usual shape, the improvement comprising fitting the helmet as follows:

(a) selecting the transverse section of the infant's cranium, parallel with a transverse plane through a supraorbital-meatal baseline, having the greatest anterior-posterior dimension and
   (i) measuring the circumference of said section to define the maximum circumference (MC) of said infant's cranium parallel to said baseline,
   (ii) defining and measuring the maximum lateral axis (ML) perpendicular to said baseline in said section,
   (iii) defining and measuring an anterior-posterior axis (AP) perpendicular to and bisecting said maximum lateral axis in said section, and
   (iv) defining and measuring the maximum chord (mc) passing through the intersection of said maximum lateral axis and said anterior-posterior axis in said section, and also the chord angle with respect to said intersection;

(b) measuring the maximum height (MH) of the infant's cranium perpendicular to said transverse plane; and (c) selecting for said infant's treatment a helmet having a cavity substantially conforming in shape to a normal infant cranium, said helmet cavity having maximum circumference, maximum lateral axis, anterior-posterior axis, maximum chord, and maximum height dimensions at least equal to and not more than about 4 cm greater than said measured values.

2. The method of claim 1 wherein the cavity of said therapeutic helmet has maximum circumference, maximum lateral axis, anterior-posterior axis, maximum chord, and maximum height dimensions at least equal to and not more than about 2 cm greater than said measured values.

3. The method of claim 1 wherein sid transverse section in step (a) is selected from a series of CT-generated transverse sections of the infant's cranium.

4. The method of claim 3 wherein said maximum height in step (b) is measured from a CT-generated horizontal scan of the infant's cranium.

5. The method of claim 1 wherein said supraorbital-meatal baseline runs through the supraorbital arch and the external auditory meatus of the infant's cranium.

6. The method of claim 1 wherein said maximum chord is selected from the group of chords passing 10°, 20°, and 30° on both sides of said anterior-posterior axis.

7. The method of claim 1 wherein said maximum chord is selected from the group of chords passing 15° and 25° on both sides of said anterior-posterior axis.

8. A graded series of sized therapeutic helmets for treatment of plagiocephaly or postoperative protection, each of the helmets having a cavity substantially conforming in shape to a normal infant cranium, the graded series comprising a plurality of helmets selected from among the following sized series in terms of helmet cavity dimensions of maximum inner circumference (MC), maximum lateral axis (ML), anterior-posterior axis (AP), maximum chord (mc), and maximum height (MH):

| Size | MC | ML | AP | mc 10° | mc 20° | mc 30° | MH |
| --- | --- | --- | --- | --- | --- | --- | --- |
| 1 | 41 | 10.7 | 14.3 | 14.25 | 13.75 | 13.5 | 9 |
| 2 | 43 | 11.3 | 14.8 | 14.75 | 14.25 | 14.0 | 10 |
| 3 | 45 | 12.0 | 15.8 | 15.75 | 15.5 | 15.25 | 10 |
| 4 | 47 | 12.7 | 16.8 | 16.5 | 16 | 15.75 | 10 |
| 5 | 49 | 13.0 | 17.3 | 17.0 | 16.75 | 16.0 | 10 |
| 6 | 51 | 13.5 | 18.4 | 18.0 | 17.5 | 17.0 | 11 | the maximum inner circumference being measured around a transverse section of the helmet cavity parallel and about 4 cm superior to a transverse plane defined by a pair of lateral baselines running through the helmet cavity regions conforming to the supraorbital arch and the external auditory meatus of the infant cranium, the maximum lateral axis being measured in the transverse section perpendicular to the lateral baselines, the anterior-posterior axis being measured in the transverse section perpendicular to and bisecting the maximum lateral axis, the maximum chord passing through the intersection of the maximum lateral axis and the anterior-posterior axis in the transverse section being measured at 10°, 20°, and 30° from the anterior-posterior axis, and the maximum inner height being measured within the confines of the helmet cavity perpendicular to the transverse plane.

9. A graded series of sized therapeutic helmets for treatment of plagiocephaly or postoperative protection, each of the helmets having a cavity substantially conforming in shape to a normal infant cranium, the graded series comprising a plurality of helmets selected from among the following sized series in terms of helmet cavity dimensions of maximum inner circumference (MC), maximum lateral axis (ML), anterior-posterior axis (AP), maximum chord (mc), and maximum height (MH):

| Size | MC | ML | AP | mc 10° | mc 20° | mc 30° | MH |
| --- | --- | --- | --- | --- | --- | --- | --- |
| 1 | 40 | 10.3 | 14.0 | 13.75 | 13.50 | 13.25 | 9 |
| 2 | 41 | 10.7 | 14.3 | 14.25 | 13.75 | 13.5 | 9 |
| 3 | 42 | 11.0 | 14.5 | 14.5 | 14.25 | 14.0 | 9 |
| 4 | 43 | 11.3 | 14.8 | 14.75 | 14.25 | 14.0 | 10 |
| 5 | 44 | 11.7 | 15.3 | 15.00 | 14.75 | 14.50 | 10 |
| 6 | 45 | 12.0 | 15.8 | 15.75 | 15.5 | 15.25 | 10 |
| 7 | 46 | 12.3 | 16.3 | 16.25 | 16 | 15.5 | 10 |
| 8 | 47 | 12.7 | 16.8 | 16.5 | 16 | 15.75 | 10 |
| 9 | 48 | 13.0 | 17.0 | 16.75 | 16.5 | 16.5 | 10 |
| 10 | 49 | 13.0 | 17.3 | 17.0 | 16.75 | 16.0 | 10 |
| 11 | 50 | 13.3 | 18.0 | 17.75 | 17.50 | 17.25 | 10 |
| 12 | 51 | 13.5 | 18.4 | 18.0 | 17.5 | 17.0 | 11 |
| 13 | 52 | 14 | 18.8 | 18.5 | 18.0 | 17.75 | 11 | the maximum inner circumference being measured around a transverse section of the helmet cavity parallel and about 4 cm superior to a transverse plane defined by a pair of lateral baselines running through the helmet cavity regions conforming to the supraorbital arch and the external auditory meatus of the infant cranium, the maximum lateral axis being measured in the transverse section perpendicular to the lateral baselines, the anterior-posterior axis being measured in the transverse section perpendicular to and bisecting the maximum lateral axis, the maximum chord passing through the intersection of the maximum lateral axis and the anterior-posterior axis in the transverse section being measured at 10°, 20°, and 30° from the anterior-posterior axis, and the maximum inner height being measured within the confines of the helmet cavity perpendicular to the transverse plane.

* * * * *

UNITED STATES PATENT AND TRADEMARK OFFICE
CERTIFICATE OF CORRECTION

PATENT NO. : 4,776,324
DATED : October 11, 1988
INVENTOR(S) : S.K. Clarren It is certified that error appears in the above-identified patent and that said Letters Patent is hereby corrected as shown below:

Column 1, line 50: after "30" insert --,-- (comma).

Column 3, line 68: "helmet" should be --helmets--.

Column 6, line 39: "18.8" should be --16.8--.

Column 7, line 57: "sid" should be --said--.

Signed and Sealed this

Fifth Day of September, 1989

*Attest:*

DONALD J. QUIGG

*Attesting Officer*    *Commissioner of Patents and Trademarks*